United States Patent [19]

Bridger et al.

[11] 4,253,982

[45] Mar. 3, 1981

[54] LUBRICANT COMPOSITIONS

[75] Inventors: Robert F. Bridger; Kirk D. Schmitt, both of Hopewell, N.J.

[73] Assignee: Mobil Oil Corporation, New York, N.Y.

[21] Appl. No.: 600,984

[22] Filed: Aug. 1, 1975

[51] Int. Cl.³ .............................................. C10M 1/32
[52] U.S. Cl. ......................... 252/51.5 R; 252/51.5 A; 252/77; 548/238
[58] Field of Search ............... 252/51.5 R, 77, 51.5 A; 260/307 F; 548/238

[56] References Cited

U.S. PATENT DOCUMENTS

| | | | |
|---|---|---|---|
| 3,966,620 | 6/1976 | Bridger et al. | 252/51.5 A |
| 4,035,309 | 7/1977 | Brois | 252/51.5 R |
| 4,153,566 | 5/1979 | Ryer | 252/51.5 R |

FOREIGN PATENT DOCUMENTS

| | | | |
|---|---|---|---|
| 1444904 | 2/1969 | Fed. Rep. of Germany | 252/51.5 A |
| 984409 | 2/1965 | United Kingdom | 252/51.5 R |

*Primary Examiner*—Andrew Metz
*Attorney, Agent, or Firm*—Charles A. Huggett; Michael G. Gilman; Howard M. Flournoy

[57] ABSTRACT

Lubricant compositions are provided containing antiwear improving amounts of a bis-oxazoline having an alkyl group containing from about 4 to about 24 carbon atoms.

14 Claims, No Drawings

LUBRICANT COMPOSITIONS

BACKGROUND OF THE INVENTION

1. Field of the Invention

This invention relates to lubricant compositions and, relates more particularly to lubricant compositions normally exhibiting poor antiwear properties under conditions of use. Still more particularly, in one of its aspects, the invention relates to lubricant compositions such as lubricating oils, automotive oils, gear oils, transmission fluids, greases and other forms of lubricants normally requiring the presence of antiwear additives.

2. Description of the Prior Art

Prior to the present invention, various antiwear additives have been suggested for use in lubricant compositions. In many applications, it was found that either the degree of improving antiwear properties was low, or that the antiwear additive, itself, was corrosive in some instances, under the conditions of use. It is therefore highly desirable that an effective additive should be both non-corrosive and capable of transmitting antiwear properties to the lubricants.

SUMMARY OF THE INVENTION

In accordance with the present invention, we have found that antiwear properties can be effectively incorporated in lubricant compositions by including an antiwear amount of a bis-oxazoline having an alkyl group containing from about 1 to about 40 carbon atoms. These bis-oxazolines are non-corrosive and effective, for example, in any of the aforementioned lubricating oils, automotive oils, gear oils, transmission fluids, greases and other forms of lubricating compositions normally requiring the presence of antiwear additives.

The bis-oxazoline antiwear additive can be effectively employed in any amount which is sufficient for imparting the desired degree of antiwear protection. In many instances, the bis-oxazoline is effectively employed in an amount from about 0.001% to about 10%, by weight, and preferably in an amount from about 0.1% to about 2%, by weight, of the total weight of the lubricant composition. Any bis-oxazoline having an alkyl group containing from about 1 to about 40 carbon atoms can be employed for improving antiwear properties of the lubricant. In many applications, bis-oxazolines having a molecular weight of from about 250 to about 900, and preferably from about 400 to about 700, are effectively employed.

The preparation of the bis-oxazoline is, in general, carried out by reacting tris(hydroxymethyl)aminomethane with an alkylsuccinic anhydride, having from about 1 to about 40 carbon atoms in the alkyl group, and preferably from about 4 to about 24 carbon atoms in the alkyl group. The tris (hydroxymethyl)aminomethane and the alkylsuccinic anhydride are reacted in a mole ratio of from about 0.5:1 to about 2:1. The reaction is, in many applications, carried out at a temperature from about 120° C. to about 250° C., and preferably at a temperature from about 160° C. to about 190° C. Exemplary of the alkylsuccinic anhydrides, having from about 1 to about 40 carbon atoms in the alkyl group are: n-octylsuccinic anhydride, n-eicosylsuccinic anhydride, n-decylsuccinic anhydride, n-dodecylsuccinic anhydride, and branched alkyl succinic anhydrides, such as those made from propylene tetramer and maleic anhydride.

It should be noted that it is critical that the alkyl group contains from about 1 to about 40 carbon atoms. If no alkyl group is present in the succinic anhydride, the final finished bis-oxazoline is insoluble in the lubricant. If the alkyl group contains more than about 40 carbon atoms, it is found that poor antiwear properties are realized.

The above-described bis-oxazoline antiwear improving agents, as previously mentioned, may be incorporated in any lubricating media which may comprise liquid hydrocarbon oils. These oils may be in the form of either a mineral oil or a synthetic oil in the form of a grease in which any of the aforementioned oils are employed as a vehicle. In general, mineral oils, employed as the lubricant, or grease vehicle, may be of any suitable lubricating viscosity range, as, for example, from about 45 SSU at 100° F. to about 6,000 SSU at 100° F., and, preferably, from about 50 to about 250 SSU at 210° F. These oils may have viscosity indexes varying from below zero to about 100 or higher. Viscosity indexes from about 70 to about 95 are preferred. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation.

In instances where synthetic oils, or synthetic oils employed as the vehicle for the grease, are desired in preference to mineral oils, or in combination therewith, various compounds of this type may be successfully utilized. Typical synthetic vehicles include polyisobutylene, polybutenes, hydrogenated polydecenes, polypropylene glycol, polyethylene glycol, trimethylol propane esters, neopentyl and pentaerythritol esters, di(2-ethyl hexyl) sebacate, di(2-ethyl hexyl) adipate, dibutyl phthalate, fluorocarbons, silicate esters, silanes, esters of phosphorous-containing acids, liquid ureas, ferrocene derivatives, hydrogenated mineral oils, chain-type polyphenyls, siloxanes and silicones (polysiloxanes), alkyl-substituted diphenyl ethers typified by a butyl-substituted bis (p-phenoxy phenyl) ether, phenoxy phenylethers, etc.

DESCRIPTION OF SPECIFIC EMBODIMENTS

The following examples and comparative data will serve to illustrate the novel bis-oxazoline additives of the present invention and the marked improvement in antiwear properties of lubricant compositions containing them.

EXAMPLE 1

Preparation of 1,2-bis[4,4-bis(hydroxymethyl)oxazolinyl]decane 10 parts n-octylsuccinic anhydride and 12 parts tris(hydroxymethyl)aminomethane were heated neat 3 hrs. at 180° C. under a rapid flow of $N_2$. The product was obtained as a colorless glass in 100% yield. The following spectral properties confirm the structure shown below: ir (neat) 3300 (OH), 1600 (C=N); nmr (CDCl$_3$) δ 4.40 (broad s, 4.0 H, 2 $CH_2$'s in rings), δ 4.25 (broad s, 3.7 H, 4 OH, addition of $D_2O$ eliminates peak), δ 3.55 (broadened 10 Hz AB, 7.2 H, 4 $CH_2O$), δ 2.5 (broad s, 3.0 H, CH—CH), δ 1.4 (broad s with t shoulder at 0.9, 17 H, n-$C_8H_{17}$).

Anal. Calcd. for $C_{20}H_{36}N_2O_6$: C, 59.97%; H, 9.06%; N, 7.00%; Found: C, 60.05%; H, 9.23%; N, 7.09%.

The above-described reaction can be illustrated as follows:

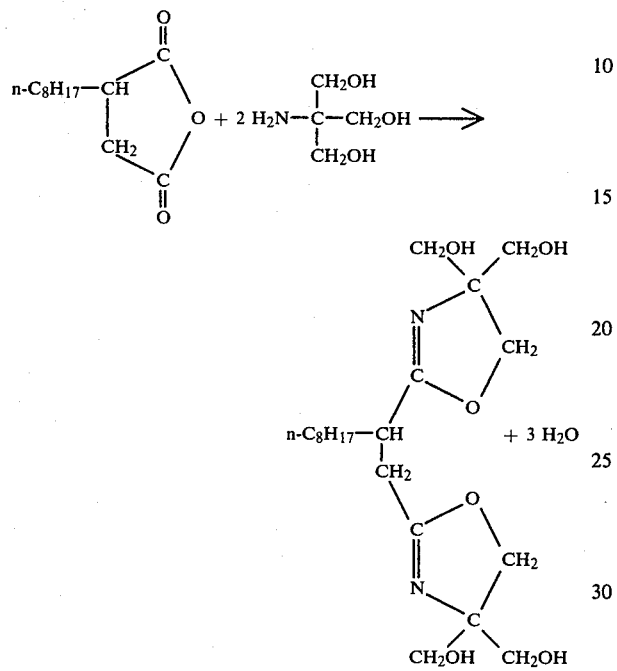

The bis-oxazoline produced is a n-octyl-bis-oxazoline and is more specifically designated as 1,2-bis[4,4-bis(hydroxymethyl)oxazolinyl]decane.

EXAMPLE 2

Preparation of 1,2-bis[4,4-bis(hydroxymethyl)oxazolinyl]decosane 19 parts n-eicosylsuccinic anhydride and 12 parts tris(hydroxymethyl) aminomethane were heated together neat until a homogeneous oil resulted, 130 parts xylene added and the mixture refluxed through a Dean-Stark trap 4 hrs. at which point 2.3 parts $H_2O$ (85%) had collected. The solvent was partially removed in vacuo and completely by heating at 100° C./0.09 mm for 1½ hr. in a Kugelrohr apparatus to give 100% of a white waxy solid easily peeled from the sides of the flask. The structure of the product was determined by the following spectral properties: ir(neat) 3300(OH), 1660(C=N,λmax); nmr(CDCl$_3$) δ 4.60 (broad s, 4.0 H, 4 OH, addition of $D_2O$ gave an emulsion), δ 4.3 (broad s, 3.7 H, 2 ring $CH_2$'s), δ 3.5 (envelope, 8 H, 4 $CH_2O$—), δ 0.8–2.8 (envelope at 1.0–1.4 with t shoulder at 1.0 with small m's at 2.0 and 2.6, 44 H, —CH—$CH_2$—and n—$C_{20}H_{41}$—).

The above-described reaction can be illustrated as follows:

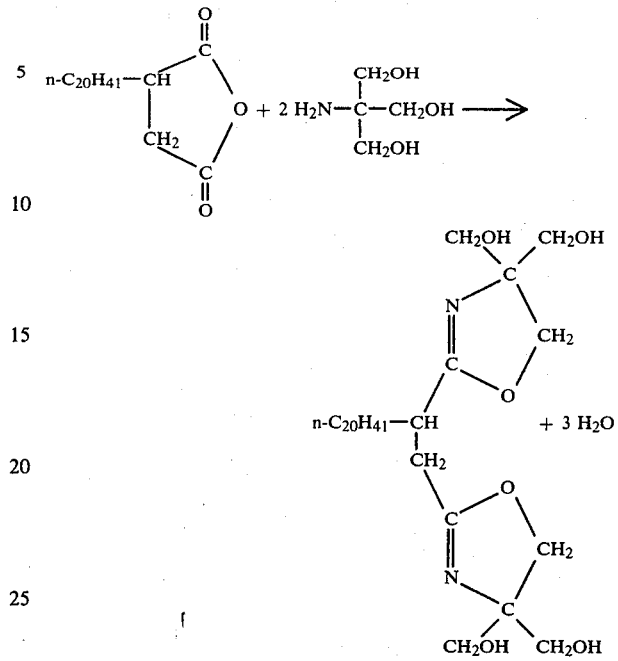

The bis-oxazoline is a n-eicosyl-bis-oxazoline and is more specifically designated as 1,2-bis[4,4-bis(hydroxymethyl)oxazolinyl]docosane.

In order to demonstrate the improvement in antiwear properties realized by employing the above-described bis-oxazolines of the present invention in lubricant compositions compared with that present in the untreated lubricant compositions, comparative data were obtained in accordance with the Standard Four-Ball Wear Test. This test is disclosed in U.S. Pat. No. 3,423,316. In general, in this test three steel balls of 52–100 steel are held in a ball cup. A fourth ball positioned on a rotatable vertical axis is brought into contact with the three balls and is rotated against them. The force with which the fourth ball is held against the three stationary balls may be varied according to a desired load. The test lubricant is added to the ball cup and acts as a lubricant for the rotation. At the end of the test, the steel balls are investigated for wear-scar; the extent of scarring represents the effectiveness of the lubricant as an antiwear agent (Table I). Results are also reported as wear rates in volume of wear per unit sliding distance per kilogram load. The lower the wear rate, the more effective the lubricant as an antiwear agent. Table II shows wear results for steel-on-bronze, in which the three stationary balls have been replaced by bronze specimens. The base stock oil employed in accordance with the test results shown in the following Tables I and II comprised a 150 SSU at 210° F. solvent-refined paraffinic bright stock lubricating oil. In the data of the following Tables, the bis-oxazoline additives are employed in concentrations of 0.02 moles per kilogram of oil. (Corresponding weight percent concentrations are shown in the tables.)

TABLE I

Four Ball Wear Test Results
Steel-on-steel
40 kg load
600 rpm
30 minutes

| Additive | Concentration mole/kg | Wt. % | Coefficient of Friction | Wear Scar Diameter nm | Wear Rate × $10^{12}$ cc/cm-kg |
|---|---|---|---|---|---|
| 200° F. | | | | | |
| None (Base Stock Only) | — | — | 0.0873 | 0.6858 | 4.60 |
| Example 1 | 0.02 | 0.8 | 0.0954 | 0.4826 | 0.94 |
| Example 2 | 0.02 | 1.14 | 0.0859 | 0.4026 | 0.35 |
| 400° F. | | | | | |
| None (Base Stock Only) | — | — | 0.1593 | 0.8341 | 10.5 |
| Example 2 | 0.02 | 1.14 | 0.0798 | 0.4445 | 0.62 |

TABLE II

Four Ball Wear Test Results
Steel-on-bronze
40 kg load
600 rpm
30 minutes

| Additive | Concentration mole/kg | Wt % | Coefficient of Friction | Wear Scar Diameter nm | Wear Rate × $10^{12}$ cc/cm-kg |
|---|---|---|---|---|---|
| None (Base Stock Only) | — | — | 0.0531 | 0.7963 | 3.87 |
| Example 2 | 0.02 | 1.14 | 0.0669 | 0.6858 | 1.92 |

It will be apparent from the data of Tables I and II that the bis-oxazolines of the present invention are markedly effective as antiwear additives. It should be noted that the steel-on-bronze experiment of Table II displayed no corrosion of the bronze specimens when the bis-oxazoline of Example 2 was used, while most conventional phosphorus-sulfur type antiwear agents cause extensive corrosion of bronze under the same experimental conditions.

While this invention has been described with reference to preferred compositions and components therefor it will be understood, by those skilled in the art, that departure from the preferred embodiments can be effectively made and are within the scope of the specification.

We claim:

1. A lubricant composition comprising an oil of lubricating viscosity or grease prepared therefrom containing a minor antiwear improving amount of a bis-oxazoline having an alkyl group containing from 4 to 24 carbon atoms wherein said bis-oxazoline is obtained by reacting tris(hydroxymethyl) aminomethane with an alkylsuccinic anhydride, having from 4 to 24 carbon atoms in the alkyl group, in a mole ratio of from about 0.5:1 to about 2:1.

2. The lubricant composition defined in claim 1 wherein the bis-oxazoline is present in an amount from about 0.001% to about 10%, by weight.

3. The lubricant composition defined in claim 1 wherein the bis-oxazoline is present in an amount from about 0.1% to about 2%, by weight.

4. The lubricant composition defined in claim 1 wherein the bis-oxazoline has a molecular weight of from about 250 to about 900.

5. The lubricant composition defined in claim 1 wherein the bis-oxazoline has a molecular weight of from about 400 to about 700.

6. The lubricant composition defined in claim 1 wherein said lubricant comprises an oil of lubricating viscosity.

7. The lubricant composition defined in claim 1 wherein said lubricant comprises a grease.

8. The lubricant composition defined in claim 1 wherein the bis-oxazoline is 1,2-bis[4,4-bis(hydroxymethyl)oxazolinyl]decane.

9. The lubricant composition defined in claim 1 wherein the bis-oxazoline is 1,2-bis[4,4-bis(hydroxymethyl) oxazolinyl]docosane.

10. The lubricant composition of claim 1 wherein said molar ratio of tris(hydroxymethyl)aminomethane to alkylsuccinic anhydride is 2:1.

11. A bis-oxazoline prepared by reacting tris(hydroxymethyl)aminomethane with an alkylsuccinic anhydride, having from 4 to 24 carbon atoms in the alkyl group, in a mole ratio of from about 0.5:1 to about 2:1.

12. The bis-oxazoline defined in claim 11 wherein said mole ratio of tris(hydroxymethyl) aminomethane to alkylsuccinic anhydride is 2:1.

13. The bis-oxazoline defined in claim 11 wherein said bis-oxazoline is 1,2-bis[4,4-bis(hydroxymethyl)oxazolinyl]decane.

14. The bis-oxazoline defined in claim 11 wherein said bis-oxazoline is 1,2-bis[4,4-bis(hydroxymethyl)oxazolinyl]docosane.